(12) United States Patent
Mohammed et al.

(10) Patent No.: US 9,618,824 B2
(45) Date of Patent: Apr. 11, 2017

(54) INTEGRATED TERAHERTZ SENSOR

(71) Applicant: Intel Corporation, Santa Clara, CA (US)

(72) Inventors: Edris M. Mohammed, Beaverton, OR (US); Ibrahim Ban, Beaverton, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/499,115

(22) Filed: Sep. 27, 2014

(65) Prior Publication Data

US 2016/0091776 A1   Mar. 31, 2016

(51) Int. Cl.
  *G02F 1/35*    (2006.01)
  *H01L 31/14*   (2006.01)
  *G01V 8/00*    (2006.01)

(52) U.S. Cl.
  CPC ............. *G02F 1/353* (2013.01); *G01V 8/005* (2013.01); *H01L 31/14* (2013.01); *G02F 2203/13* (2013.01)

(58) Field of Classification Search
  CPC ...................................................... G02F 1/353
  See application file for complete search history.

(56) References Cited

U.S. PATENT DOCUMENTS

| 2007/0073115 | A1 | 3/2007 | Hwang et al. |
| 2010/0219421 | A1 | 9/2010 | Murphy et al. |
| 2010/0305460 | A1 | 12/2010 | Pinter et al. |
| 2010/0314545 | A1* | 12/2010 | Logan, Jr. ................. G01J 3/10 250/339.07 |
| 2011/0257536 | A1 | 10/2011 | Ser et al. |
| 2012/0044479 | A1* | 2/2012 | Roulston ................. G01J 3/108 356/51 |
| 2012/0051386 | A1* | 3/2012 | Kim ..................... H01S 5/1096 372/96 |
| 2012/0068090 | A1* | 3/2012 | Park .................... H01S 5/06258 250/493.1 |
| 2013/0320215 | A1* | 12/2013 | Park ..................... H04B 10/801 250/340 |
| 2014/0166881 | A1* | 6/2014 | Han .................... G01N 21/3581 250/338.1 |
| 2014/0346357 | A1* | 11/2014 | Jarrahi .................... H01L 31/09 250/338.4 |

OTHER PUBLICATIONS

C. Lin, James, "Microwave sensing of physiological movement and volume change: A review", Bioelectromagnetics, vol. 13(6), 557-65, 1992, 1 Page of Abstract Only.

(Continued)

*Primary Examiner* — Christine Sung
(74) *Attorney, Agent, or Firm* — Jordan IP Law, LLC (57) ABSTRACT

Systems and methods may provide for an integrated miniature sensor that operates in the Terahertz region of the electromagnetic spectrum. The integrated miniature sensor may detect a remote target and operate in a non-contact, non-invasive manner. Numerous signal analysis techniques may be employed such as Doppler radar technology, absorption spectroscopy, and others when the integrated miniature sensor is used in biomedical, physiological and other settings where prolonged recording of bio-signals is needed.

17 Claims, 5 Drawing Sheets

(56) References Cited

OTHER PUBLICATIONS

Massar, Melody L., "Time-Frequency Analysis of Terahertz Radar Signals for Rapid Heart and Breath Rate Detection", Thesis, Air Force Institute of Technology, AFIT/GAM/ENC/08-05, Jun. 2008, 81 Pages.
Llombart et al., "Silicon Micromachined Lens Antenna for THz Integrated Heterodyne Arrays", IEEE Transactions on Terahertz Science and Technology, vol. 3, No. 5, Sep. 2013, pp. 515-523.
Zouaghi et al., "Broadband terahertz spectroscopy: principles, fundamental research and potential for industrial applications", European Journal of Physics, vol. 34, S179, Published on Oct. 22, 2013, 1 Page of Abstract Only.
International Search Report and Written Opinion for PCT Application No. PCT/US20151048505, mailed Dec. 16, 2015, 15 pages.
Office Action for Taiwanese Patent Application No. 104127520, dated Dec. 29, 2016, 16 pages including 8 pages of English translation.

\* cited by examiner

INTEGRATED TERAHERTZ SENSOR

TECHNICAL FIELD

Embodiments generally relate to Terahertz sensors. More particularly, embodiments relate to integrated and miniaturized sensors that transmit and detect electromagnetic wave signals in the Terahertz electromagnetic spectrum to a remote target.

BACKGROUND

Conventional approaches to taking electrocardiogram (ECG) measurements may involve attaching wet (e.g., Ag/AgCl) based electrodes on the surface of the skin of the patient. Heart activity may then be recorded or displayed by a device external to the body. The attachment and removal of the electrodes may be inconvenient and/or painful to the patient, as well as time consuming to the medical professional administering the measurement.

Similarly, conventional blood glucose monitoring solutions may involve piercing the skin (typically, on the finger) to draw blood, then applying the blood to a chemically active disposable test strip. A device may then analyze the test strip to determine the glucose level in the blood. Such an approach may be considered invasive as it involves piercing the skin, which may occur many times per day for certain Diabetes patients. Simply put, conventional ECG and blood glucose techniques may require an invasive method to acquire the signals, as well as bulky and awkward sensors.

BRIEF DESCRIPTION OF THE DRAWINGS

The various advantages of the embodiments will become apparent to one skilled in the art by reading the following specification and appended claims, and by referencing the following drawings, in which:

DESCRIPTION OF EMBODIMENTS

Figure 1:
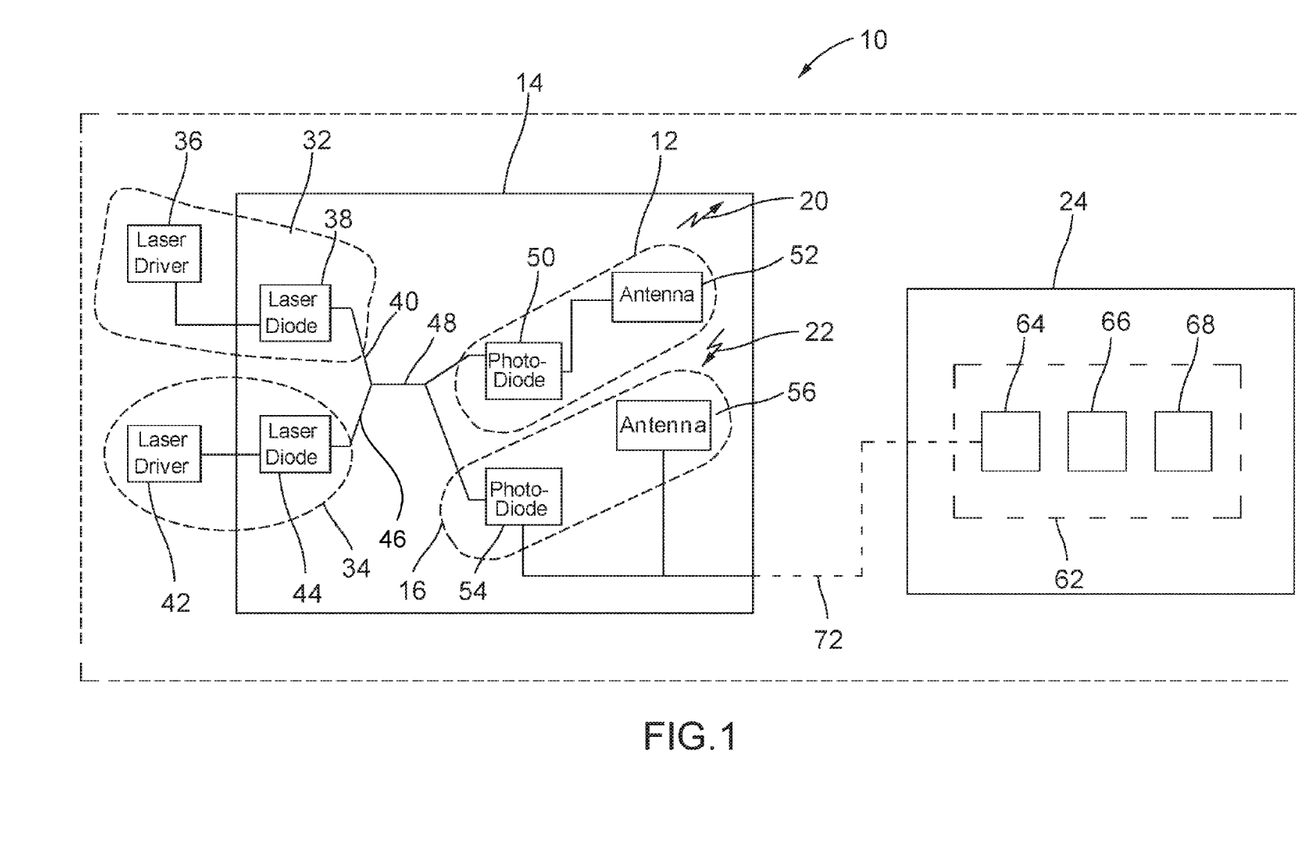
FIG. 1 is a block diagram of an example of a Terahertz sensing system according to an embodiment.

Turning now to FIG. 1, a Terahertz (THz) sensing system 10 is shown, wherein a first photomixer 12 integrated in an optical module 14 transmits an outbound electromagnetic wave signal 20 in the Terahertz region of the electromagnetic spectrum. The optical module 14 may include a first laser 32 and a second laser 34 to excite the first photomixer 12. In this embodiment, the first laser 32 utilizes a first laser driver 36 and a first laser diode 38 to generate a first signal 40 with a frequency. The second laser 34 may include a second laser driver 42 and a second laser diode 44 to generate a second signal 46 with a frequency. The first and second lasers 32, 34 may be aligned to a 2×2 3 dB waveguide coupler 48 to produce optical beat signals in each arm. The optical beat signal coming out of the first arm excites the first photomixer 12. The first photomixer 12 may include a first conductive component 50 that can produce an oscillating photocurrent (not shown) when excited. Photomixing may include heterodyne difference frequency generation in high bandwidth photoconductors. The output of two continuous-wave lasers can convert into terahertz radiation, at the difference frequency between the first and second signals 40, 46. A photomixer may include either a photoconductive component with metal-semiconductor-metal (MSM) interface, or a p-i-n photodiode. GaAs-based terahertz devices often use the former configuration, whereas InGaAs/InP emitters use a pin structure. The laser irradiation may create electron-hole pairs in a semiconductor. Applying a bias voltage may then generate a photocurrent that oscillates at a "beat frequency".

A first antenna 52 associated with the first photoconductive component 50 may translate the oscillating photocurrent (not shown) into the transmitted outbound electromagnetic wave signal 20 in the Terahertz region. A first lens 58 (see FIG. 3) may be associated with the first antenna 52 and the first photomixer 12 to collimate and direct the outbound electromagnetic wave signal 20 to the remote target 18 (see FIGS. 2A and 2B). The lens 58 (see FIG. 3) may be directly deposited on the first antenna 52 at the first photomixer 12. Additionally, the lens 58 (see FIG. 3) may be one of a discrete molded unit or a discrete micro-machined unit. The illustrated outbound electromagnetic wave signal 20 contacts the remote target 18 (see FIGS. 2A and 2B) and is reflected back as an inbound electromagnetic wave signal 22 in the Terahertz region.

A second photomixer 16 may be integrated in the optical module 14 to detect the inbound electromagnetic wave signal 22 in the Terahertz region that is generated by the outbound electromagnetic wave signal 20 reflecting from the remote target 18 (see FIG. 2). The second photomixer 16 may include a second photoconductive component 54 and a second antenna 56 to detect the inbound reflected electromagnetic wave signal 22 in the Terahertz region. A second lens (not shown) may be associated with the second antenna 56 to focus the inbound electromagnetic wave signal 22 in the Terahertz region.

An integrated electrical module 24 may be coupled 72 to the optical module 14 and may include a processor 62 to process the inbound electromagnetic wave signal 22 in the Terahertz region. The electrical module 24 may be an integrated chip. The lens 58 (see FIG. 3) that may be used to collimate the outbound electromagnetic wave signal 20, may be coupled 72 to the electrical module 24 and formed in the back side of the integrated chip using a standard semiconductor process. The electrical module 24 may include laser driver circuitry (not shown), data amplification circuitry 64, filtering circuitry 66, and analog to digital conversion circuitry 68 to assist with the processing of the inbound and outbound electromagnetic wave signals 22,20.

Figure 2A:
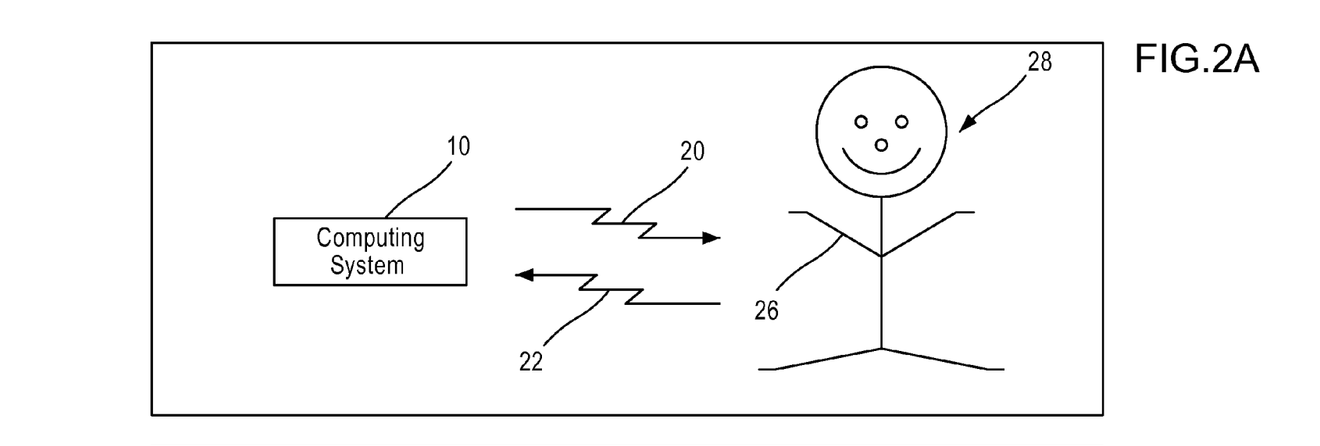
FIGS. 2A-2B are illustrations of examples of signal analysis applications according to embodiments.
Figure 2B:
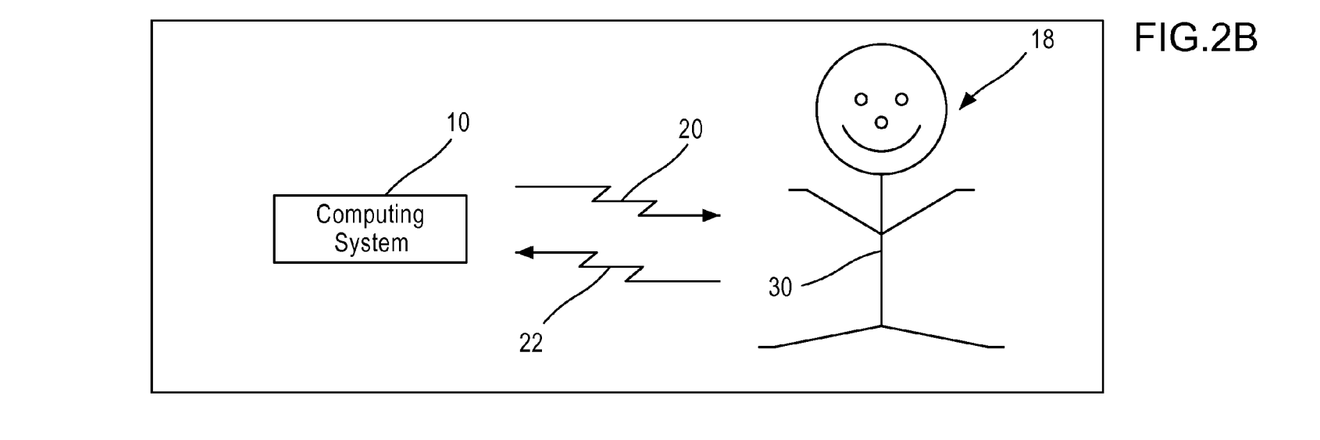

FIGS. 2A-2B demonstrate that a variety of scientific technologies may be used by the second photomixer 16 to assist with the detection of the inbound electromagnetic wave signal 22. For example, FIG. 2A describes a situation where the skin and soft tissue 26 are used as a remote target 28. In this embodiment, the second photomixer 16 (FIG. 1) uses absorption spectroscopy to detect blood glucose levels. Blood glucose is a way of testing the concentration of glucose in the blood (glycemia) in diabetes patients. In FIG. 2A, the detection is based on absorption spectroscopy where the Terahertz signal is absorbed by the patient's skin or soft tissue. Both reflection and transmission spectroscopy may be used to determine the blood glucose level. The illustrated detection approach shows a high sensitivity to blood glucose level in the capillaries. In this embodiment, the interaction with the skin or soft tissue is remote and in a non-contact manner.

In FIG. 2B, the embodiment describes a situation where a patient's chest 30 is the remote target 18. In this example, the second photomixer 16 (FIG. 1), employs Doppler radar technology to detect and assist with the determination of heart rate, respiration rate and heart activity as in an electrocardiogram. ECG which is the recording of the electrical activity of the heart of a patient to determine vital medical signs, as heart rate, and causes of symptoms of heart disease. In this example, an integrated and miniaturized electro-optical device emits an electromagnetic wave in the Terahertz region to remotely detect ECG and heart rate of a person from distances ranging from a few centimeters to several meters. The detection, based on the Doppler radar theory, includes a target with a periodic movement that reflects the transmitted signal with its phase modulated by the time-varying position of the target. When the target is the person's chest, the reflected signal may contain information about the chest displacement due to heartbeat and respiration. Not only ECG, but respiration rate may also be extracted from the movement of the chest. Hence, the vital signs such as heart and respiratory rates can be detected remotely and in a non-contact manner. In addition, this embodiment may be embedded in fabrics, walls, etc. for continuous monitoring of vital signs or for human presence detection.

Figure 3:
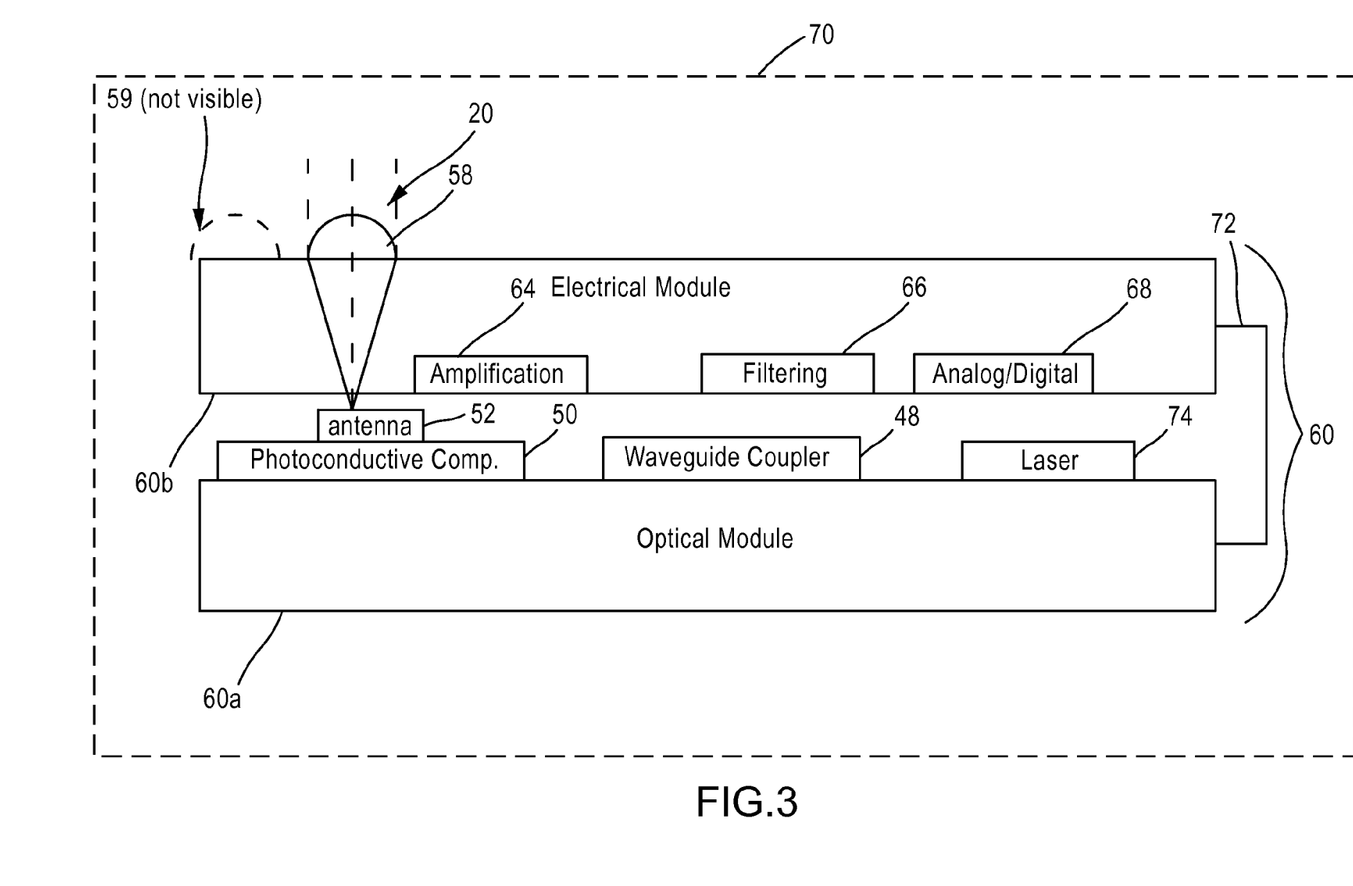
FIG. 3 is a side view of an example of a miniature remote Terahertz sensor according to an embodiment.

Turning now to FIG. 3, a miniature remote sensor 70 is shown wherein the sensor 70 includes an integrated chip 60 (60a, 60b) having both an optical module 60a and an electrical module 60b. The optical module 60a may have a similar structure and/or functionality to that of the optical module 14 (FIG. 1) and the electrical module 60b may have a similar and/or functionality to that of the electrical module 24 (FIG. 1), previously discussed. In FIG. 3, both the optical and electrical modules 60a, 60b may be integrated on substrates that form the integrated chip 60. The optical module 60a may be coupled 72 to the electrical module 60b by using wire bonding. The optical module 60a may also be coupled to the electrical module 60b by a flip-chip bonding technique. The optical module 60a may include lenses 58 and 59 to collimate/focus the transmitted outbound/received inbound electromagnetic wave signals 20 and 22 in the Terahertz region. The lenses 58 and 59 may also be discrete units and decoupled (not shown) from the integrated chip 60. The first antenna 52 may be in direct association with the first photoconductive component 50 to collimate the outbound electromagnetic wave signal 20 through the lens 58 situated on the electrical module 60b. The illustrated electrical module 60b includes the circuitry for laser driver (not shown) and data amplification 64, filtering 66, and analog to digital conversion 68. More circuit functional blocks may be added to the electrical chip 60b such as the processor 62 (see FIG. 1) to control the aforementioned electrical functions.

Figure 4:
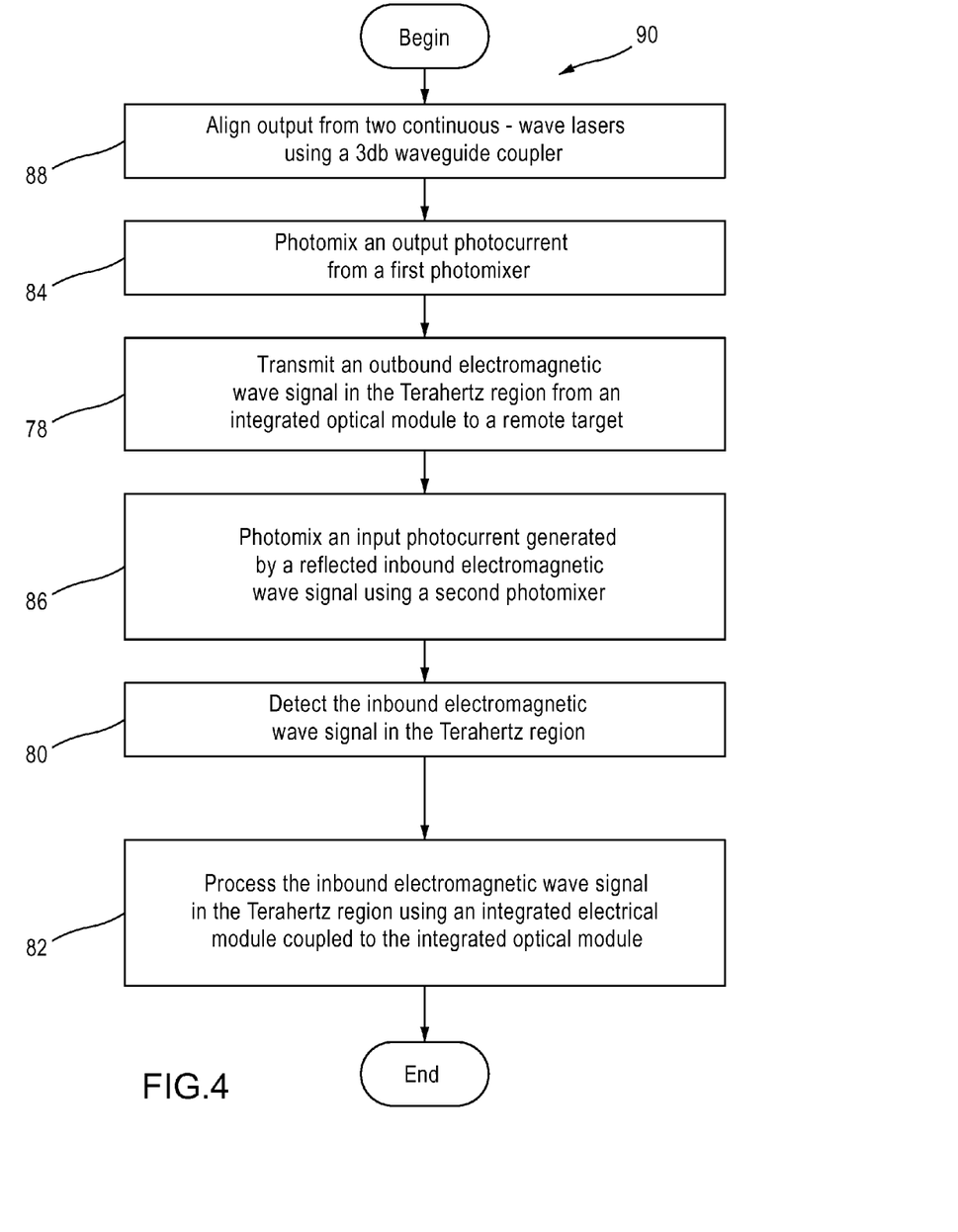
FIG. 4 is a flowchart of an example of a method of interacting with a sensor according to an embodiment.

FIG. 4 lists a method 90 of interacting with a Terahertz sensor. The method 90 may be implemented in a sensing system 10 such as that already described in FIG. 1. More particularly, the method 90 may be implemented as one or more modules in a set of logic instructions stored in a machine- or non-transitory computer-readable storage medium and include random access memory (RAM), read only memory (ROM), programmable ROM (PROM), firmware, flash memory, etc., in configurable logic such as, for example, programmable logic arrays PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (ICMOS) or transistor-transistor logic (TTL) technology, or any combination thereof.

Illustrated processing block 88 aligns output from two continuous wave lasers by using the 3 dB waveguide coupler previously discussed. In block 84, the output from block 88 is transmitted to the first photomixer and photomixed to produce the outbound electromagnetic wave signal in the Terahertz region. In block 78, the outbound electromagnetic wave signal is transmitted to a remote target. In block 86, the outbound electromagnetic wave is reflected back from the remote target as an inbound electromagnetic wave signal and is photomixed by the second photomixer. The detection of the inbound electromagnetic wave signal in the Terahertz region may be accomplished in block 80 by using the second photomixer associated with the electrical module. The electrical module processes the inbound electromagnetic wave signal detected by the second photomixer as depicted in illustrated block 82, to produce a discernable output. The electrical module may include the appropriate data amplification, filtering and analog to digital conversion circuitry to perform the processing of the inbound electromagnetic wave signal.

Figure 5:
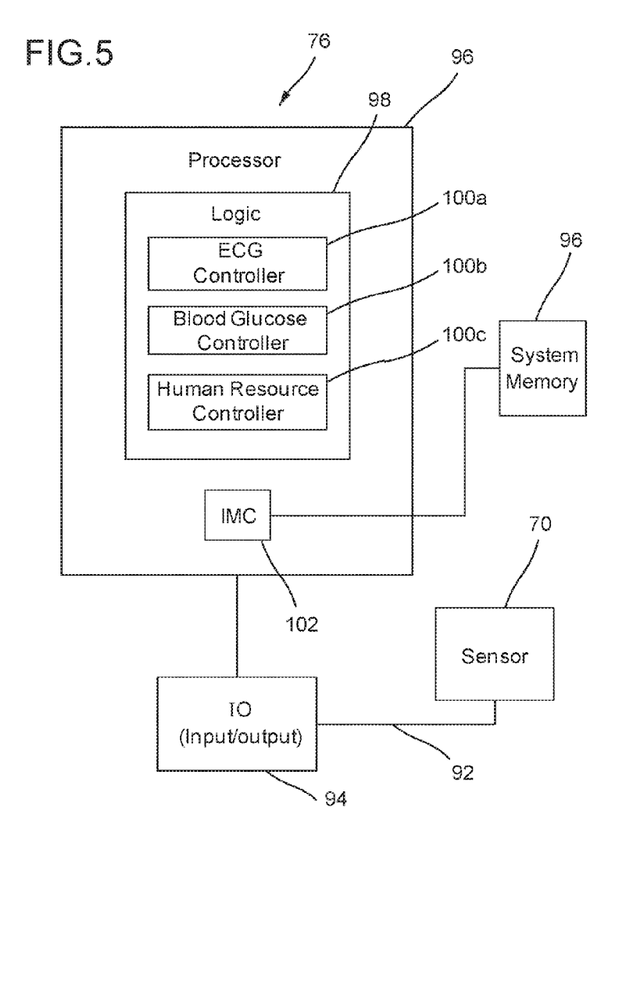
FIG. 5 is a flowchart of an example of a closed loop logic architecture according to an embodiment.

FIG. 5 shows a computing system 76 that may be part of a network that processes the inbound and outbound electromagnetic wave signals 22, 20. In the illustrated example, the miniature remote sensor 70 may be used to detect ECG and heart rate of a person using an ECG controller 100a for processing, blood glucose levels of a person using a blood glucose controller 100b for processing, and continuous monitoring of vital signs of a person such as heart and respiratory rates using a human presence controller 100c for processing. A signal 92 from the miniature remote sensor 70 may be transmitted to an input/output (IO) module 94. The illustrated IO module 94 functions as a host controller and communicates with a system processor 96 that may include logic 98. Depending upon an intended purpose, the logic 98 may engage the ECG controller 100a, the blood glucose controller 100b, or the human presence controller 100c to process the signal from the IO module 94. The IO module 94 may include one or more hardware circuit blocks (e.g., smart amplifiers, analog to digital conversion, integrated sensor hub) to support signal processing functionality. System memory 96 may include double data rate (DDR) synchronous dynamic random access memory (SDRAM, e.g., DDR3 SDRAM JEDEC Standard JESD79-3C, April 2008) modules. The modules of the system memory 96 may be incorporated into a single inline memory module (SIMM), dual inline memory module (DIMM), small outline DIMM (SODIMM), and so forth. An integrated memory controller (IMC) 102 may be used to communicate with the system memory 96.

ADDITIONAL NOTES AND EXAMPLES

Example 1 may include a computing system to control an integrated Terahertz sensor, comprising a first photomixer integrated in an optical module to transmit an outbound electromagnetic wave signal in the Terahertz region to a remote target, a second photomixer integrated in the optical module to detect an inbound electromagnetic wave signal in the Terahertz region generated by the outbound electromagnetic wave signal reflecting from the remote target, and an electrical module coupled to the optical module to process the inbound electromagnetic wave signal.

Example 2 may include the computing system of Example 1, wherein the optical module includes a first laser and a second laser to excite the first photomixer.

Example 3 may include the computing system of Example 2, wherein the first laser includes a first laser driver and a first diode to generate a first signal with a frequency.

Example 4 may include the computing system of Example 2, wherein the second laser includes a second laser driver and a second laser diode to generate a second signal with a frequency.

Example 5 may include the computing system of Example 2, wherein the optical module includes a 3 dB waveguide coupler that aligns the first and second lasers.

Example 6 may include the computing system of Example 1, wherein the first photomixer includes a first photoconductive component that produces an oscillating photocurrent, and a first antenna that translates the oscillating photocurrent into the transmitted outbound electromagnetic wave signal in the Terahertz region.

Example 7 may include the computing system of Example 1, wherein the second photomixer includes a second photoconductive component and a second antenna to detect the inbound reflected electromagnetic wave signal in the Terahertz region.

Example 8 may include the computing system of Example 1, wherein the optical module includes first and second lenses to collimate/focus the transmitted outbound/inbound electromagnetic wave signals.

Example 9 may include the computing system of Example 8, wherein the first and second lenses are coupled to the electrical module.

Example 10 may include the computing system of Examples 7 or 8, wherein the first and second lenses are ones of a discrete molded unit or a discrete micro-machined unit.

Example 11 may include the computing system of Example 1, wherein the electrical module is an integrated chip with a processor that includes laser driver circuitry, data amplification circuitry, filtering circuitry, and analog to digital conversion circuitry.

Example 12 may include the computing system of Example 1, wherein the second photomixer is to use absorption spectroscopy to determine blood glucose levels associated with skin and soft tissue of a patient.

Example 13 may include the computing system of Example 1, wherein the second photomixer is to use Doppler radar technology to determine heart rate, respiration rate, and electrocardiogram activity associated with a person's chest.

Example 14 may include a miniature remote sensor comprising an optical module to transmit an outbound electromagnetic wave signal in the Terahertz region and detects an inbound reflected electromagnetic wave signal in the Terahertz region from the target, an electrical module to process both the transmitted and the reflected electromagnetic wave signals in the Terahertz region, and a coupling connecting the optical module and the electrical module.

Example 15 may include the remote sensor of Example 14, wherein the coupling is a wire bonding.

Example 16 may include the remote sensor of Examples 13 or 14, wherein the coupling is a flip-chip bonding.

Example 17 may include the remote sensor of Example 14, wherein the optical module further comprises first and second lenses to collimate/focus the transmitted outbound/inbound electromagnetic wave signals in the Terahertz region.

Example 18 may include a method to interact with a sensor comprising transmitting an outbound electromagnetic wave signal in the Terahertz region from an integrated optical module to a remote target, detecting an inbound electromagnetic wave signal in the Terahertz region generated by the outbound electromagnetic wave signal reflecting from the remote target, and processing the inbound electromagnetic wave signal in the Terahertz region that was generated by the outbound electromagnetic wave signal reflected from the remote target, in an integrated electrical module coupled to the optical module.

Example 19 may include the method of Example 18, further comprising generating the transmitted outbound electromagnetic wave signal by photomixing an output photocurrent from a first photomixer.

Example 20 may include the method of Example 18, further comprising detecting the reflected inbound electromagnetic wave signal by photomixing an input photocurrent from a second photomixer.

Example 21 may include the method of Example 18, further comprising generating the transmitted outbound electromagnetic wave signal by aligning output from two continuous-wave lasers using a 3 dB waveguide coupler.

Example 22 may include at least one non-transitory computer-readable storage medium comprising a set of instructions which, when executed by a computing system, cause the computing system to transmit an outbound electromagnetic wave signal in the Terahertz region from an integrated optical module to a remote target, detect an inbound electromagnetic wave signal in the Terahertz region generated by the outbound electromagnetic wave signal reflecting from the remote target, and process the inbound electromagnetic wave signal in the Terahertz region that was generated by the outbound electromagnetic wave signal reflecting from the remote target, in an integrated electrical module coupled to the optical module.

Example 23 may include the at least one non-transitory computer-readable storage medium of Example 22, wherein the instructions, when executed, generate the transmitted electromagnetic wave signal by photomixing an output photocurrent from a first photomixer.

Example 24 may include the at least one non-transitory computer-readable storage medium of Example 22, wherein the instructions, when executed, detect the reflected inbound electromagnetic wave signal by photomixing an input photocurrent from a second photomixer.

Example 25 may include the at least one non-transitory computer-readable storage medium of Example 22, wherein the instructions, when executed, generate the transmitted outbound electromagnetic wave signal by aligning output from two continuous-wave lasers using a 3 dB waveguide coupler.

Thus, the aforementioned techniques can provide remote detection of an electromagnetic wave signal in the Terahertz region reflected from a target in a non-contact manner. Detection can be based on Doppler radar theory, absorption spectroscopy etc. to assist in the area of biomedical sensing and physiological research, especially when prolonged recording of bio-signals is needed.

Embodiments are applicable for use with all types of semiconductor integrated circuit (IC) chips. Examples of these IC chips include but are not limited to processors, controllers, chipset components, programmable logic arrays, memory chips, network chips, systems on chips (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g. photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first," "second," etc. may be used herein only to facilitate discussion, and carry no particular temporal or chronological significance unless otherwise indicated.

As used in this application and in the claims, a list of items joined by the term "one or more of" may mean any combination of the listed terms. For example, the phrases "one or more of A, B or C" may mean A, B, C; A and B; A and C; B and C; or A, B and C.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and the following claims.

We claim:

1. An electromagnetic sensing system comprising:
a first photomixer integrated in an optical module to transmit an outbound electromagnetic wave signal in the Terahertz region to a remote target;
a second photomixer integrated in the optical module to detect an inbound electromagnetic wave signal in the Terahertz region generated by the outbound electromagnetic wave signal reflecting from the remote target; and
an electrical module coupled to the optical module to process the inbound electromagnetic wave signal,
wherein the optical module includes a first laser and a second laser to excite the first photomixer, and a 2×2 3 dB waveguide coupler that aligns the first laser and the second laser.

2. The system of claim 1, wherein the first laser includes a first laser driver and a first laser diode to generate a first signal with a frequency.

3. The system of claim 1, wherein the second laser includes a second laser driver and a second laser diode to generate a second signal with a frequency.

4. The system of claim 1, wherein the first photomixer includes a first photoconductive component that produces an oscillating photocurrent, and a first antenna that translates the oscillating photocurrent into the transmitted outbound electromagnetic wave signal in the Terahertz region.

5. Them system of claim 1, wherein the second photomixer includes a second photoconductive component and a second antenna to detect the inbound reflected electromagnetic wave signal in the Terahertz region.

6. The system of claim 1, wherein the optical module includes first and second lenses to collimate/focus the transmitted outbound/inbound electromagnetic wave signals.

7. The system of claim 6, wherein the first and second lenses are coupled to the electrical module.

8. The system of claim 6, wherein the first and second lenses are ones of a discrete molded unit or a discrete micro-machined unit.

9. The system of claim 1, wherein the electrical module is an integrated chip with a processor that includes laser driver circuitry, data amplification circuitry, filtering circuitry and analog to digital conversion circuitry.

10. The system of claim 1, wherein the second photomixer is to use absorption spectroscopy to determine blood glucose levels associated with skin and soft tissue of a patient.

11. The system of claim 1, wherein the second photomixer is to use Doppler radar technology to determine heart rate, respiration rate, and electrocardiogram activity associated with a person's chest.

12. A method of interacting with a sensor, comprising:
transmitting an outbound electromagnetic wave signal in the Terahertz region from an integrated optical module to a remote target;
detecting an inbound electromagnetic wave signal in the Terahertz region generated by the outbound electromagnetic wave signal reflecting from the remote target; and
processing the inbound electromagnetic wave signal in the Terahertz region that was generated by the outbound electromagnetic wave signal reflected from the remote target, in an integrated electrical module coupled to the optical module,
wherein the outbound electromagnetic wave signal is to be generated by aligning outputs from two continuous-wave lasers using a 2×2 3 dB waveguide coupler.

13. The method of claim 12, further comprising generating the transmitted outbound electromagnetic wave signal by photomixing an output photocurrent from a first photomixer.

14. The method of claim 12, further comprising detecting the reflected inbound electromagnetic wave signal by photomixing an input photocurrent from a second photomixer.

15. At least one non-transitory computer-readable storage medium comprising a set of instructions, which when executed by a computing system, cause the computing system to:

transmit an outbound electromagnetic wave signal in the Terahertz region from an integrated optical module to a remote target;

detect an inbound electromagnetic wave signal in the Terahertz region generated by the outbound electromagnetic wave signal reflecting from the remote target; and process the inbound electromagnetic wave signal in the Terahertz region that was generated by the outbound electromagnetic wave signal reflecting from the remote target, in an integrated electrical module coupled to the optical module, wherein the outbound electromagnetic wave signal is to be generated by aligning outputs from two continuous-wave lasers using a 2×2 3 dB waveguide coupler.

16. The at least one non-transitory computer-readable storage medium of claim 15, wherein the instructions, when executed, generate the transmitted electromagnetic wave signal by photomixing an output photocurrent from a first photomixer.

17. The at least one non-transitory computer-readable storage medium of claim 15, wherein the instructions, when executed, detect the reflected inbound electromagnetic wave signal by photomixing an input photocurrent from a second photomixer.

* * * * *